(12) United States Patent
Hatakeda et al.

(10) Patent No.: US 7,045,622 B2
(45) Date of Patent: May 16, 2006

(54) PROCESS FOR PRODUCING LACTAM

(75) Inventors: Kiyotaka Hatakeda, Miyagi (JP); Osamu Sato, Miyagi (JP); Yutaka Ikushima, Miyagi (JP); Kazuo Torii, Miyagi (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 119 days.

(21) Appl. No.: 10/469,533

(22) PCT Filed: Mar. 23, 2001

(86) PCT No.: PCT/JP01/02321

§ 371 (c)(1),
(2), (4) Date: Sep. 8, 2003

(87) PCT Pub. No.: WO02/070474

PCT Pub. Date: Sep. 12, 2002

(65) Prior Publication Data

US 2004/0097726 A1 May 20, 2004

(30) Foreign Application Priority Data

Mar. 7, 2001 (JP) ............................. 2001-063358

(51) Int. Cl.
*C07D 201/04* (2006.01)
*C07D 223/10* (2006.01)

(52) U.S. Cl. ...................................... 540/535; 540/536
(58) Field of Classification Search ................ 540/535, 540/536

See application file for complete search history.

(56) References Cited

FOREIGN PATENT DOCUMENTS

JP 10-287644 10/1998

OTHER PUBLICATIONS

Yutaka Ikushima, et al., Journal of the American Chemical Society, vol. 122, No. 9, pp. 1908-1918 2000.
Osamu Sato, et al., The Journal of Organic Chemistry, vol. 63, No. 24, pp. 9100-9102.

*Primary Examiner*—Bruck Kifle
(74) *Attorney, Agent, or Firm*—Oblon, Spivak, McClelland, Maier & Neustadt, P.C.

(57) ABSTRACT

It is an object of the present invention to provide a method of continuously producing a lactam in high-temperature high-pressure water, and the present invention relates to a method for producing a lactam characterized by selectively synthesizing the lactam without bringing about hydrolysis by introducing an oxime into flowing high-temperature high-pressure water, wherein the lactam is continuously synthesized at a high rate from the oxime in water at a high temperature of at least 250° C. and a high pressure of at least 12 MPa.

6 Claims, 2 Drawing Sheets

PROCESS FOR PRODUCING LACTAM

BACKGROUND OF THE INVENTION

1. Field of the Invention

The present invention relates to a method of continuously producing a lactam from an oxime in high-temperature high-pressure water, and more particularly to a novel continuous production method of continuously producing a lactam by carrying out a rearrangement reaction of an oxime in high-temperature high-pressure water without a catalyst. Yet more specifically, there is provided a method that is favorable and useful as an industrial technique, enabling production of a lactam without the need for treatment to neutralize a large amount of used waste sulfuric acid as seen in the case of a conventional production method in which concentrated sulfuric acid is used as a catalyst.

2. Description of the Related Art

Conventionally, a lactam such as E-caprolactam, which is used as a raw material of nylon 6, is industrially produced by a Beckmann rearrangement from a carbonyl compound oxime such as cyclohexanone oxime. An acid catalyst is used in this rearrangement reaction, and because the reaction is carried out while boiling, hydrolysis of the oxime will be brought about by the presence of even a very small amount of water in the system, resulting in a drop in the yield of the lactam. To prevent this, the usual method is to carry out the reaction while boiling, using fuming sulfuric acid as the acid catalyst. With this method, because the reaction is carried out under harsh conditions, there are known to be problems with regard to corrosion of the materials of the apparatus, the hazardousness of the production process, and processing of the byproduct ammonium sulfate. When recovering the lactam, the sulfuric acid used must be neutralized with ammonia, and more than 2 kg of ammonium sulfate is produced as a byproduct per 1 kg of the lactam. Ammonium sulfate has little commercial value, and hence it is difficult to utilize the ammonium sulfate, and thus it has become necessary to process the ammonium sulfate.

In recent years, fears over deterioration of the global environment have heightened, and in the chemical industry there have been calls for the development of environmentally friendly chemical processes that are simple and efficient, according to which reaction can be completed within a short time, and according to which harmful substances are not used or not discharged. Regarding lactam production, there have been calls for the development of a novel production process that is efficient, is not accompanied by byproducts, and does not use concentrated sulfuric acid, with which there are problems in terms of corrosion of the materials of the apparatus, operational safety, and the environment.

As methods for resolving the above-problems, two methods have been proposed in which reaction is carried out in high-temperature high-pressure water and an acid catalyst such as sulfuric acid is not used at all, namely (1) a batch type synthesis method (O. Sato, Y. Ikushima and T. Yokoyama, Journal of Organic Chemistry 1998, 63, 9100–9102), and (2) a flow type synthesis method (Y. Ikushima, K. Hatakeda, O. Sato, T. Yokoyama and M. Arai, Journal of American Chemical Society 2000, 122, 1908–1918).

With the batch type synthesis method (1), a reaction is carried out for 3 minutes to obtain the product, wherein cyclohexanone oxime is sealed in a stainless steel tube of internal volume 10 ml, the stainless steel tube is put into a salt bath to rise the temperature thereof to 200 to 400° C. within 30 seconds. It is considered that this method is not suitable as a mass production process, but nevertheless the method has attracted attention as a synthesis method that does not use an acid catalyst such as fuming sulfuric acid. Operation of the reaction is carried out intermittently to completion one batch at a time, and it takes a time of approximately 20 to 30 seconds to raise the temperature to the set reaction temperature. There is thus a drawback in that a large amount of cyclohexanone as the hydrolysis product is produced while the temperature is being raised, and hence the yield of the targeted $\epsilon$-caprolactam is reduced. Moreover, cyclohexanone is a raw material of cyclohexanone oxime, and hence the reaction goes in the reverse direction, which is fatal for an industrial process.

With the flow type synthesis method (2), operation of the reaction is carried out continuously and hence it is considered that the method is suitable for mass production, but a cyclohexanone oxime aqueous solution at room temperature is heated to produce the high-temperature high-pressure carrier water in the reaction, and hence it seems that raising the temperature up to the set reaction temperature takes a long time. Accordingly, in an experiment in which reaction was carried out for 113 seconds under conditions of 350° C. and 22.1 MPa, it was revealed that only cyclohexanone was obtained as a product, with $\epsilon$-caprolactam not being produced at all. Moreover, it is reported that the reaction is carried out even under conditions of 374.5° C., $\epsilon$-caprolactam and cyclohexanone are both produced. Consequently, it seems that, as with the batch type synthesis method (1), it takes time to raise the temperature, and hence cyclohexanone is produced through hydrolysis of the cyclohexanone oxime while the temperature of the solvent water is passing from, for example, 100 to 300° C., and thus there is a drawback in that the yield of the targeted $\epsilon$-caprolactam is reduced.

SUMMARY OF THE INVENTION

It is an object of the present invention to provide a method of continuously producing a lactam in high-temperature high-pressure water.

The present invention relates to a method of producing a lactam characterized by selectively synthesizing the lactam by introducing an oxime into flowing high-temperature high-pressure water without bringing about hydrolysis thereof, wherein the lactam is continuously synthesized at a high rate from the oxime in water at a high temperature of at least 250° C. and a high pressure of at least 12 MPa.

Amid the situation described above and in view of the prior art described above, the present inventors carried out various studies into a method of producing a lactam from an oxime in high-temperature high-pressure water, and through this process discovered that to continuously and efficiently produce a lactam from an oxime in high-temperature high-pressure water, it is important to raise the temperature of the oxime to the set reaction temperature within a short time; the present inventors then carried out further studies based on this finding, thus accomplishing the present invention.

That is, the present invention was accomplished with an object of providing a method of selectively producing a lactam without producing cyclohexanone, by introducing an oxime as a substrate into high-temperature high-pressure water, thus carrying out reaction with the time taken to raise the temperature of the substrate shortened.

The synthesis method of the present invention, which was developed by the present inventors through various experiments, is, for example, a method of producing caprolactam selectively and more efficiently and in a shorter time than with a conventional method, comprising continuously introducing an oxime aqueous solution or an oxime directly into a reaction zone in which there exists high-temperature high-pressure water, whereby a set reaction temperature is reached within a short time, and hence hydrolysis of the oxime is suppressed.

To resolve the problems described above, the present invention is constituted from the following technical means.

(1) A method for producing a lactam, comprising introducing oxime into high-temperature high-pressure water, raising the temperature of the oxime to put the oxime into a prescribed high-temperature high-pressure state within a short time, and subjecting the oxime to a rearrangement reaction to obtain the lactam.

(2) The method for producing a lactam according to (1), wherein a substrate aqueous solution having the oxime dissolved therein is introduced into the continuously flowing high-temperature high-pressure water, thus subjecting the oxime to the reaction in the prescribed high-temperature high-pressure state.

(3) The method for producing a lactam according to (1), wherein molten oxime is introduced into the continuously flowing high-temperature high-pressure water, thus subjecting the oxime to the reaction in the prescribed high-temperature high-pressure state.

(4) The method for producing a lactam according to any one of (1) through (3), wherein the oxime is subjected to the reaction in the high-temperature high-pressure water at a temperature of at least 250° C. and a pressure of at least 12 MPa.

(5) The method for producing a lactam according to any one of (1) through (4), wherein the temperature of the oxime is raised to put the oxime into the prescribed high-temperature high-pressure state within a short time of not more than 3 seconds and the oxime is subjected to the reaction.

(6) The method for producing a lactam according to any one of (1) through (5), wherein the oxime is subjected to the reaction in the prescribed high-temperature high-pressure state for a time of not more than 60 seconds.

(7) The method for producing a lactam according to any one of (1) through (6), wherein the oxime is cyclohexanone oxime.

Following is a more detailed description of the present invention.

To facilitate explanation of the present invention, a detailed description will be given taking as an example the case of producing a lactam by introducing an oxime aqueous solution into high-temperature high-pressure water, whereby a reaction temperature of 250 to 450° C. is reached within a short time of not more than 3 seconds, and reaction takes place under a reaction pressure of 12 to 40 MPa.

The production method of the present invention, which was developed by the present inventors through various experiments, is, for example, a method in which a cyclohexanone oxime aqueous solution is continuously introduced into a reaction zone through which high-temperature high-pressure water is flowing, whereby the temperature thereof is made to reach a set reaction temperature within a short time of not more than 3 seconds, and hence ε-caprolactam is synthesized through a rearrangement reaction of the cyclohexanone oxime, without bringing about hydrolysis. In the present invention, high-temperature high-pressure water is used as the reaction zone or reaction solvent; organic solvents and catalysts such as sulfuric acid are not used, and do not need to be used. Consequently, according to the present method, waste matter that must be processed such as waste solvent, waste catalyst and/or ammonium sulfate is not discharged. Moreover, there is no production of cyclohexanone through hydrolysis of the cyclohexanone oxime. Unreacted raw material can be reused in the reaction of the present invention. Furthermore, with the method of the present invention, the product can be produced efficiently, continuously, and at a high rate, and hence the method of the present invention is considered to be the best means of producing lactams.

Following is a description of the method of producing a lactam of the present invention.

In the present invention, for example, an oxime aqueous solution or an oxime is continuously introduced directly into a reaction zone in which there exists high-temperature high-pressure water, whereby the temperature thereof is made to reach a set reaction temperature within a short time, and hence a lactam can be produced efficiently with a shorter reaction time than with a conventional method, and selectively with hydrolysis of the oxime being suppressed.

An oxime used as the substrate raw material in the present invention is represented by general formula (1) (chemical formula 1), wherein n is an integer from 1 to 9, and $R_1$ is hydrogen or an alkyl group. As an alkyl group, any having 1 to 20 carbon atoms can be used, for example a methyl group, an ethyl group, a propyl group or a butyl group. An example of the oxime is cyclohexanone oxime, but the present invention is not limited to this.

Chemical formula 1

A lactam obtained in the present invention is represented by general formula (2) (chemical formula 2), wherein n is an integer from 1 to 9, and $R_1$ is hydrogen or an alkyl group. As an alkyl group, any having 1 to 20 carbon atoms can be used, for example a methyl group, an ethyl group, a propyl group or a butyl group.

Chemical formula 2

The lactam obtained in the present invention is a many-membered ring lactam having at least five members in the ring, for example a 5-membered ring lactam, a 6-membered ring lactam or a 7-membered ring lactam. Examples include ε-caprolactam, γ-butyrolactam, γ-valerolactam and δ-valerolactam, but the present invention is not limited to these.

As a specific example of the production of a lactam according to the present invention, that is an example in which a 7-membered ring lactam is produced, general formula (3) (chemical formula 3) shows the reaction formula for synthesizing ε-caprolactam from cyclohexanone oxime.

Chemical formula 3

CYCLOHEXANONE OXIME

ε-CAPROLACTAM

It is known that the synthesis of a lactam through a Beckmann rearrangement of an oxime proceeds in the presence of an acid catalyst The fact that a lactam can be synthesized as in the present invention through a Beckmann rearrangement of an oxime in high-temperature high-pressure water is interesting matter. It can be conjectured that in high-temperature high-pressure water it may be that an acid catalyst function appears through production of protons, polarization of the water molecule structure, or the like, and it is expected that this will be verified through physico-chemical studies into high-temperature high-pressure water in the future.

According to the present invention, the oxime that is the substrate can be put into a prescribed high-temperature high-pressure state within a short time, and hence hydrolysis can be suppressed, and thus a lactam can be produced selectively. Note, however, that a small amount of an amino acid is produced through the present reaction. For example, in the case of synthesizing ε-caprolactam from cyclohexanone oxime by reacting for 0.667 seconds under a high temperature of 375° C. and high pressure of 30 MPa, the yield of ε-caprolactam was 41.4%, and compared with this yield 6-aminocaproic acid was obtained at a yield of 0.3%. Conversion of 6-aminocaproic acid into ε-caprolactam is relatively easy, and this reaction also proceeds in high-temperature high-pressure water. In the above reaction, the hydrolysis product cyclohexanone was not detected at all.

As the water used as the raw material of the high-temperature high-pressure water in the present invention, distilled water, ion exchange water, tap water, ground water and so on can be favorably used. When using such a water as the raw material of the high-temperature high-pressure water, in particular in the case of using the high-temperature high-pressure water in a super critical state, dissolved oxygen may cause oxidative decomposition of organic matter, and hence it is preferable to use the water after removing the dissolved oxygen in advance by bubbling with nitrogen gas or the like. In the case of using the high-temperature high-pressure water in a subcritical state, there is no particular need to remove dissolved oxygen from the raw material water, although this may be done.

The temperature of the high-temperature high-pressure water used in the present invention can be controlled using a heater, molten salt or the like outside the reactor. Alternatively, this temperature control can be carried out using an internal heat means inside the reactor. Moreover, it is also possible to produce the high-temperature high-pressure water in advance, and inject the high-temperature high-pressure water into the reactor from the outside using a conveying pump or the like for carrying out the reaction. It is also possible to feed two or more types of high-temperature high-pressure water having different temperatures and pressures to one another into the reaction system, whereby the reaction conditions can be controlled. In the case that the flow system is used, the pressure inside the reaction vessel can be controlled using a pressure regulating valve. Furthermore, the pressure can also be controlled by injecting in another gas such as nitrogen gas. In general the pressure used should be at least the self-generated pressure at the temperature used.

Basically, the present invention is realized so long as the reaction is carried out in high-temperature high-pressure water at a temperature of at least 250° C. and a pressure of at least 12 MPa. The present invention can be attained more favorably if the reaction is carried out in high-temperature high-pressure water at a temperature of at least 300° C. and a pressure of at least 15 MPa. Furthermore, the present invention can be attained most favorably if the reaction is carried out in high-temperature high-pressure water at a temperature of at least 350° C. and a pressure in a range of 15 MPa to 40 MPa. The ideal temperature varies according to the processing time, but in general a temperature in a range of 300° C. to 450° C. can be favorably selected. Moreover, an appropriate temperature and pressure can be adopted in accordance with the throughput and the type of the reaction apparatus. With the present invention, it has been found that the reaction tends to proceed better if the temperature is higher, and moreover that the reaction also tends to be promoted somewhat by the pressure being higher.

As the reaction apparatus, for example a high-temperature high-pressure reaction apparatus can be used; however, there is no limitation thereto, but rather any type of apparatus can be used so long as the reaction can be carried out in high-temperature high-pressure water. Here, as examples of suitable reaction apparatuses, a flow type high-temperature high-pressure reaction apparatus and flow type high-temperature high-pressure reaction apparatus capable of introducing a molten oxime are used in the present invention.

In the present invention, an oxime aqueous solution or an oxime at, for example, room temperature is directly introduced into flowing high-temperature high-pressure water, and hence the temperature of the high-temperature high-pressure water drops upon the mixing. The extent of the drop in temperature upon the mixing varies according to the initial temperature of the carrier water, the reaction pressure, the flow rate of the carrier water, the flow rate of introduction of the oxime aqueous solution or oxime, the amount introduced of the oxime, the type of the reactor, the volume of the reactor and so on. In general, from experience the set reaction temperature can be controlled by suitably selecting the initial temperature of the carrier water to be approximately 5 to 300° C. higher than the set reaction temperature.

The most distinctive feature of the present invention is that by directly introducing the oxime into high-temperature high-pressure water at a temperature approximately 5 to 300° C. higher than the set reaction temperature as described above, the time taken for the temperature of the oxime to rise to the set reaction temperature can be made to be a short time of not more than 3 seconds. Due to this, hydrolysis of the oxime can be suppressed, and as a result the selectivity and yield of the lactam can be improved. The time taken for the temperature of the oxime to rise to the set reaction temperature is more preferably not more than 1 second, yet more preferably not more than 0.5 seconds, most preferably not more than 0.3 seconds.

In the case of using the carrier water in a super critical state in particular, the viscosity of the fluid is lower and the diffusion coefficient is higher compared with that of general liquid carrier water, and hence it is thought that the mixing rate is dramatically increased. Moreover, it is known that with high-temperature high-pressure water above a subcritical state close to the super critical point, the dielectric constant is reduced and the solubility of organic substances increases dramatically; it is thus thought that the solubility of oximes similarly increases, resulting in conditions suitable for the rearrangement reaction.

The reaction conditions vary according to the type and concentration of the oxime to be used, the volume of the reactor tube, the conditions of the high-temperature high-pressure water, and so on. In the present invention, there is no limitation to using one oxime in the reaction, but rather the reaction will still proceed favorably even if a mixture of two or more oximes is used. The oxime can be melted and introduced into the high-temperature high-pressure water and thus dissolved therein, or a powder of the oxime may be directly introduced into the high-temperature high-pressure water. Alternatively, a substrate aqueous solution in which the oxime has been dissolved in advance at room temperature can be introduced into the high-temperature high-pressure water.

The concentration of the oxime to be introduced into the reactor can be controlled by controlling the flow rate of the high-temperature high-pressure water to be used as the flowing carrier water and the flow rate of introduction of the reaction substrate oxime. In general, the concentration of the oxime to be introduced into the reactor is selected from a concentration range of 1 mM to 10 M. It is preferable to select a suitable concentration value from 2 mM to 5 M, and most preferable to select a suitable concentration value from 2 mM to 2 M, although there is no limitation to these concentration ranges in the present invention.

In the present invention, the reaction yield of the lactam can be manipulated by adjusting the temperature and pressure of the reaction system, the internal diameter of the reactor, the volume of the reactor, the flow rates, the concentration of the reaction substrate, the reaction time and so on, this being in accordance with the type of the oxime.

Regarding the reaction system in the present invention, the reaction substrate oxime need merely be made to be present in high-temperature high-pressure water at a temperature of at least 250° C. and a pressure of at least 12 MPa as described above; at this time, there is no particular need to add, for example, metal ions, a water-soluble catalyst such as an acid or a base, a metal-supporting catalyst, a solid catalyst such as a solid acid or a solid base, an enzyme, or the like, and moreover there is also no need to use an organic solvent.

Basically, the most distinctive feature of the present invention is that a lactam is synthesized from an oxime by making a reaction substrate as described above be present in high-temperature high-pressure water, without a catalyst, and without an organic solvent being involved in the reaction; nevertheless, if necessary, it is quite acceptable to add an organic solvent such as methanol, ethanol or ethylene glycol, metal ions, a water-soluble catalyst such as an acid or a base, a metal-supporting catalyst, a solid catalyst such as a solid acid or a solid base, or an enzyme when carrying out the reaction.

In the present invention, using the reaction system described above, a lactam is synthesized from an oxime within a short time, i.e. with a reaction time of, for example, 0.001 seconds to 60 seconds. In the case of using a flow type reaction apparatus, the reaction time can be controlled by controlling,the reaction temperature, the reaction pressure, the flow rate of the high-temperature high-pressure water, the flow rate of introduction of the reaction substrate, the shape of the reactor, the internal diameter of the reactor, the length of the flow path of the reactor, and so on. The reaction time is more preferably selected from a range of 0.01 seconds to 30 seconds, and is most preferably selected from a range of 0.05 seconds to 10 seconds, although there is no limitation to these ranges in the present invention.

As shown in the examples described later, using a high performance liquid chromatography-mass spectrometry (LC-MS) apparatus, a nuclear magnetic resonance (NMR) spectrometer and a Fourier transform infrared (FTIR) spectrophotometer, the present inventors have verified that it is possible to carry out a rearrangement reaction from an oxime to a lactam within a short time (e.g. a reaction time of approximately 1 second) in high-temperature high-pressure water. Furthermore, by using an LC-MS apparatus, the types of the oxime, the lactam, and the byproduct amino acid can be identified, and the contents thereof can be measured accurately. Moreover, by subjecting the continuously obtained lactam to separation and purification using an ion exchange resin column, measuring the infrared absorption spectrum using an FTIR spectrophotometer, and comparing with the infrared absorption spectra of high-purity special grade reagent products, the lactam can be identified accurately. Similarly, the type and purity of the lactam can also be verified by NMR spectroscopy. The structure of the lactam can be verified using a gas chromatography-mass spectrometry (GC-MS) apparatus, an LC-MS apparatus, an NMR spectrometer, and an FTIR spectrophotometer.

The reaction yield of the lactam produced in the present invention varies according to the reaction conditions such as the temperature and the pressure, the type of the oxime, the concentration of the oxime, the form of the reaction apparatus, the size of the reactor, the flow rate of the carrier water, the rate of introduction of the oxime, the reaction time, and so on. For example, in the case of $\epsilon$-caprolactam, the reaction yield was from 5.5% to 76.3%. The $\epsilon$-caprolactam is recovered mixed together with the raw material cyclohexanone oxime. Similarly, according to the present invention, any of various lactams obtained from any of various oximes or a mixture thereof are recovered together with the raw material substrates, but by using, for example, a cation exchange resin, an anion exchange resin, or a combination thereof, the lactam and the raw material substrate oxime can be separated, and moreover in the case of obtaining a plurality of lactams the lactams can be separated from one another, and hence the lactams can be purified and concentrated type by type. Moreover, the oximes recovered at the same time can be reused as raw material.

It is thus possible to synthesize lactam by subjecting oxime to a rearrangement reaction in high-temperature high-pressure water, and subject the reaction solution obtained to an ion exchange resin to separate and purify the lactam, whereby high-purity lactam can be favorably produced.

In the present invention, a prescribed concentration of an oxime is introduced as a reaction substrate into high-temperature high-pressure water, thus raising the temperature of the reaction substrate within a short time, and carrying out reaction in a prescribed high-temperature high-pressure aqueous state, whereby, for example, $\epsilon$-caprolactam is synthesized from cyclohexanone oxime. Moreover, by continuously introducing such oximes into flowing high-temperature high-pressure water, various lactams corresponding to the respective oximes can be synthesized continuously.

As described above, the present invention is a novel continuous lactam production method that enables any of various lactams to be produced continuously within a short time using the reaction system described above by adjusting the reaction conditions, the type of the reaction substrate oxime, and the concentration of the oxime, and is thus useful as a lactam production method.

DESCRIPTION OF THE PREFERRED EMBODIMENTS

Following is a concrete description of the present invention through examples; however, the present invention is not limited whatsoever by the following examples.

EXAMPLE 1

Figure 1:
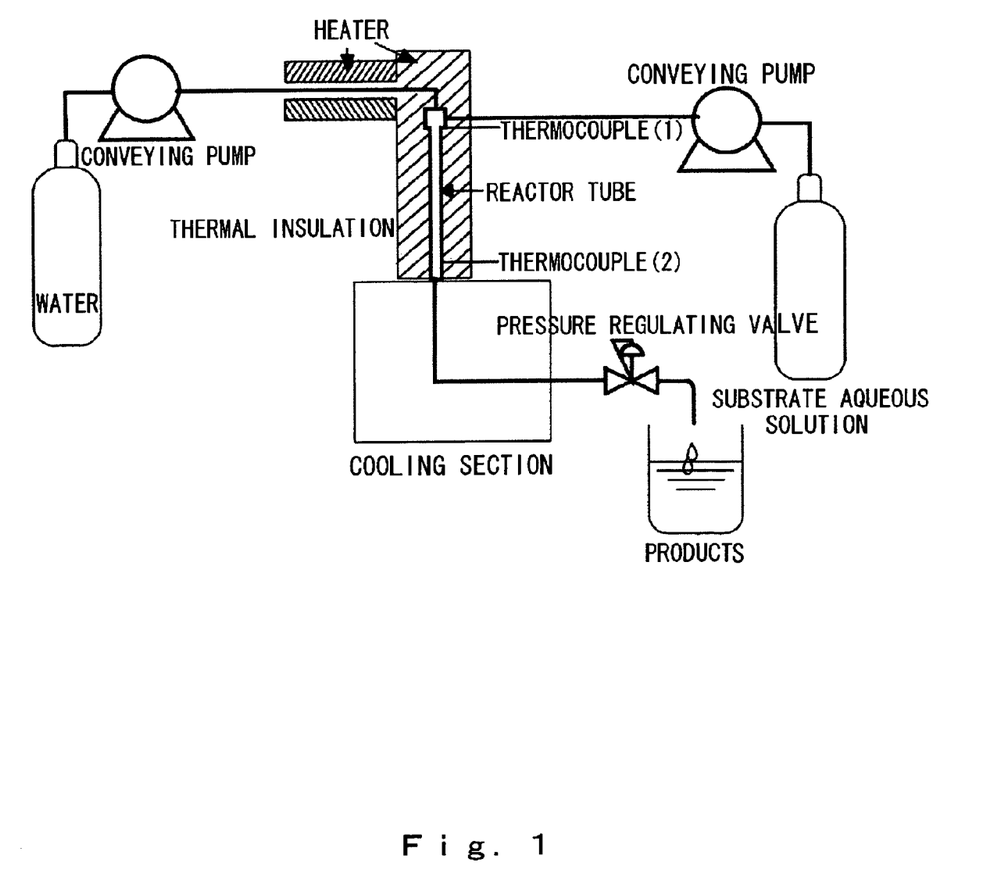
FIG. 1 shows an arrangement of a flow type high-temperature high-pressure reaction apparatus having two conveying pumps used in the present invention.

Using a continuous type high-temperature high-pressure reaction apparatus as shown in FIG. 1, continuous production of ε-caprolactam through a rearrangement reaction was attempted using a cyclohexanone oxime (purity 97%) made by Aldrich Chemical Company, Inc. in high-temperature high-pressure water of temperature 375° C., pressure 30 MPa and density 0.5583 g/cm$^3$.

The material of the reactor was alloy C-276, and the internal diameter of the reactor was 0.325 mm and the length of the reactor was 120 cm, and hence the volume of the reactor was calculated to be 0.0995 cm$^3$. Each of the prepared liquids to be introduced (i.e. the carrier water and the cyclohexanone oxime substrate solution) was injected in using a high-pressure pump. Distilled water from which dissolved oxygen had been driven out by bubbling with nitrogen gas was heated to produce carrier water at 460° C. and 30 MPa, and the carrier water was passed through at a flow rate of 3.8 ml/min. A 21.9 mM cyclohexanone oxime substrate solution was prepared using similarly deoxygenated distilled water. The substrate solution was introduced at room temperature and 30 MPa into the carrier water at the reactor inlet at a flow rate of 1.3 ml/min, thus mixing the substrate solution and the carrier water together. The reaction temperature of the mixed solution measured by a thermocouple (1) installed 1 cm from the reactor inlet was 375° C., which matched the temperature measured by a thermocouple (2) at the reactor outlet, and hence it is inferred that the temperature throughout the reactor was constant, and that the carrier water and the substrate solution were mixed together homogeneously. The substrate concentration after the mixing was 5.58 mM. The reaction time was 0.667 seconds. It is thus inferred that the mixing took place within a short time of not more than 0.006 seconds. The aqueous solution recovered after the reaction was examined using a high performance liquid chromatography-mass spectrometry apparatus, whereupon it was found that ε-caprolactam as a main product and 6-aminocaproic acid as a byproduct had been produced. Apart from that, only unreacted cyclohexanone oxime was detected, with cyclohexanone, which is the hydrolysis product of the raw material, not being detected at all. The concentration of the ε-caprolactam was 2.31 mM, and hence the reaction yield thereof was 41.4%. The concentration of the 6-aminocaproic acid was 0.017 mM, and hence the reaction yield thereof was 0.3%.

EXAMPLE 2

Reaction was carried out as in Example 1, thus attempting continuous production of ε-caprolactam through a rearrangement reaction of cyclohexanone oxime. The reaction conditions, however, were changed to the following.

Reaction Conditions
Temperature and pressure of carrier water: 404° C., 25 MPa
Flow rate of carrier water: 3.7 ml/min
Temperature and pressure of 21.9 mM substrate solution: 25° C., 25 MPa
Flow rate of 21.9 mM substrate solution: 1.3 ml/min
Temperature of high-temperature high-pressure water to be reacted: 350° C.
Pressure of high-temperature high-pressure water to be reacted: 25 MPa
Density of high-temperature high-pressure water to be reacted: 0.6257 g/cm$^3$
Flow rate of high-temperature high-pressure water to be reacted: 5.0 ml/min The cyclohexanone oxime substrate concentration after the mixing was 5.69 mM. The reaction time was 0.747 seconds, and the temperature throughout the reactor was constant, and hence it is inferred that the mixing took place within a short time of not more than 0.006 seconds. The aqueous solution after the reaction was examined using a high performance liquid chromatography-mass spectrometry apparatus, whereupon it was found that ε-caprolactam as a main product and 6-aminocaproic acid as a byproduct had been produced. Apart from that, only unreacted cyclohexanone oxime was detected, with cyclohexanone, which is the hydrolysis product of the raw material, not being detected at all. The concentration of the ε-caprolactam was 1.61 mM, and hence the reaction yield thereof was 28.3%. The concentration of the 6-aminocaproic acid was 0.011 mM, and hence the reaction yield thereof was 0.2%.

EXAMPLE 3

Reaction was carried out as in Example 1, thus attempting continuous production of ε-caprolactam through a rearrangement reaction of cyclohexanone oxime. The reaction conditions, however, were changed to the following.

Reaction Conditions
Temperature and pressure of carrier water: 352° C., 15 MPa
Flow rate of carrier water: 2.9 ml/min
Temperature and pressure of 21.9 mM substrate solution: 25° C., 15 MPa
Flow rate of 21.9 mM substrate solution: 2.1 ml/min
Temperature of high-temperature high-pressure water to be reacted: 300° C.
Pressure of high-temperature high-pressure water to be reacted: 15 MPa
Density of high-temperature high-pressure water to be reacted: 0.7259 g/cm$^3$
Flow rate of high-temperature high-pressure water to be reacted: 5.0 ml/min The cyclohexanone oxime substrate concentration after the mixing was 9.20 mM. The reaction time was 0.867 seconds, and the temperature throughout the reactor was constant, and hence it is inferred that the mixing together of the carrier water and the substrate solution took place within a short time of not more than 0.007 seconds. The aqueous solution after the reaction was examined using a high performance liquid chromatography-mass spectrometry apparatus, whereupon it was found that ε-caprolactam had been produced as a product. Apart from that, only unreacted cyclohexanone oxime was detected, with cyclohexanone, which is the hydrolysis product of the raw material, not being detected at all. The concentration of the $\epsilon$-caprolactam was 0.51 mM, and hence the reaction yield thereof was 5.5%.

COMPARATIVE EXAMPLE 1

Reaction was carried out as in Example 1, thus attempting continuous production of $\epsilon$-caprolactam through a rearrangement reaction of cyclohexanone oxime. The reaction conditions, however, were changed to the following.

Reaction Conditions
Temperature and pressure of carrier water: 314° C., 15 MPa
Flow rate of carrier water: 3.5 ml/min
Temperature and pressure of 21.9 mM substrate solution: 25° C., 15 MPa
Flow rate of 21.9 mM substrate solution: 1.4 ml/min
Temperature of high-temperature high-pressure water to be reacted: 200° C.
Pressure of high-temperature high-pressure water to be reacted: 15 MPa
Density of high-temperature high-pressure water to be reacted: 0.8746 g/cm$^3$
Flow rate of high-temperature high-pressure water to be reacted: 4.9 ml/min The cyclohexanone oxime substrate concentration after the mixing was 6.26 mM. The reaction time was 1.066 seconds, and the temperature throughout the reactor was constant, and hence it is inferred that the mixing together of the carrier water and the substrate solution took place within a short time of not more than 0.009 seconds. The aqueous solution after the reaction was examined using a high performance liquid chromatography-mass spectrometry apparatus, whereupon production of $\epsilon$-caprolactam was not detected at all.

COMPARATIVE EXAMPLE 2

Reaction was carried out as in Example 1, thus attempting continuous production of $\epsilon$-caprolactam through a rearrangement reaction of cyclohexanone oxime. The reaction conditions, however, were changed to the following.

Reaction Conditions
Temperature and pressure of carrier water: 345° C., 9 MPa
Flow rate of carrier water: 3.3 ml/min
Temperature and pressure of 21.9 mM substrate solution: 25° C., 9 MPa
Flow rate of 21.9 mM substrate solution: 1.7 ml/min
Temperature of high-temperature high-pressure water to be reacted: 300° C.
Pressure of high-temperature high-pressure water to be reacted: 9 MPa
Density of high-temperature high-pressure water to be reacted: 0.7134 g/cm$^3$
Flow rate of high-temperature high-pressure water to be reacted: 5.0 ml/min The cyclohexanone oxime substrate concentration after the mixing was 7.45 mM. The reaction time was 0.852 seconds, and the temperature throughout the reactor was constant, and hence it is inferred that the mixing together of the carrier water and the substrate solution took place within a short time of not more than 0.007 seconds. The aqueous solution after the reaction was examined using a high performance liquid chromatography-mass spectrometry apparatus, whereupon production of $\epsilon$-caprolactam was not detected at all.

EXAMPLE 4

Reaction was carried out as in Example 1, thus attempting continuous production of $\epsilon$-caprolactam through a rearrangement reaction of cyclohexanone oxime. The reaction conditions, however, were changed to the following.

Reaction Conditions
Temperature and pressure of carrier water: 550° C., 25 MPa
Flow rate of carrier water: 4.6 ml/min
Temperature and pressure of 21.9 mM substrate solution: 25° C., 25 MPa
Flow rate of 21.9 mM substrate solution: 0.5 ml/min
Temperature of high-temperature high-pressure water to be reacted: 400° C.
Pressure of high-temperature high-pressure water to be reacted: 25 MPa
Density of high-temperature high-pressure water to be reacted: 0.1666 g/cm$^3$
Flow rate of high-temperature high-pressure water to be reacted: 5.1 ml/min The cyclohexanone oxime substrate concentration after the mixing was 2.15 mM. The reaction time was 0.195 seconds, and the temperature throughout the reactor was constant, and hence it is inferred that the mixing took place within a short time of not more than 0.002 seconds. The aqueous solution after the reaction was examined using a high performance liquid chromatography-mass spectrometry apparatus, whereupon it was found that $\epsilon$-caprolactam as a main product and 6-aminocaproic acid as a byproduct had been produced. Apart from that, only unreacted cyclohexanone oxime was detected, with cyclohexanone, which is the hydrolysis product of the raw material, not being detected at all. The concentration of the $\epsilon$-caprolactam was 0.19 mM, and hence the reaction yield thereof was 8.8%. The concentration of the 6-aminocaproic acid was 0.002 mM, and hence the reaction yield thereof was 0.1%.

EXAMPLE 5

Reaction was carried out as in Example 1, thus attempting continuous production of $\epsilon$-caprolactam through a rearrangement reaction of cyclohexanone oxime. The reaction conditions, however, were changed to the following.

Reaction Conditions
Temperature and pressure of carrier water: 550° C., 40 MPa
Flow rate of carrier water: 3.7 ml/min
Temperature and pressure of 21.9 mM substrate solution: 25° C., 40 MPa
Flow rate of 21.9 mM substrate solution: 1.3 ml/min
Temperature of high-temperature high-pressure water to be reacted: 400° C.
Pressure of high-temperature high-pressure water to be reacted: 40 MPa
Density of high-temperature high-pressure water to be reacted: 0.5237 g/cm$^3$
Flow rate of high-temperature high-pressure water to be reacted: 5.0 ml/min The cyclohexanone oxime substrate concentration after the mixing was 5.69 mM. The reaction time was 0.625 seconds, and the temperature throughout the reactor was constant, and hence it is inferred that the mixing took place within a short time of not more than 0.005 seconds. The aqueous solution after the reaction was examined using a high performance liquid chromatography-mass spectrometry apparatus, whereupon it was found that ε-caprolactam as a main product and 6-aminocaproic acid as a byproduct had been produced. Apart from that, only unreacted cyclohexanone oxime was detected, with cyclohexanone, which is the hydrolysis product of the raw material, not being detected at all. The concentration of the ε-caprolactam was 3.78 mM, and hence the reaction yield thereof was 66.4%. The concentration of the 6-aminocaproic acid was 0.078 mM, and hence the reaction yield thereof was 1.4%.

EXAMPLE 6

Reaction was carried out as in Example 1, thus attempting continuous production of ε-caprolactam through a rearrangement reaction of cyclohexanone oxime. The reaction conditions, however, were changed to the following.

Reaction Conditions
Temperature and pressure of carrier water: 550° C., 40 MPa
Flow rate of carrier water: 4.2 ml/min
Temperature and pressure of 21.9 mM substrate solution: 25° C., 40 MPa
Flow rate of 21.9 mM substrate solution: 0.8 ml/min
Temperature of high-temperature high-pressure water to be reacted: 420° C.
Pressure of high-temperature high-pressure water to be reacted: 40 MPa
Density of high-temperature high-pressure water to be reacted: 0.4238 g/cm$^3$
Flow rate of high-temperature high-pressure water to be reacted: 5.0 ml/min The cyclohexanone oxime substrate concentration after the mixing was 3.50 mM. The reaction time was 0.506 seconds, and the temperature throughout the reactor was constant, and hence it is inferred that the mixing took place within a short time of not more than 0.004 seconds. The aqueous solution after the reaction was examined using a high performance liquid chromatography-mass spectrometry apparatus, whereupon it was found that ε-caprolactam as a main product and 6-aminocaproic acid as a byproduct had been produced. Apart from that, only unreacted cyclohexanone oxime was detected, with cyclohexanone, which is the hydrolysis product of the raw material, not being detected at all. The concentration of the ε-caprolactam was 1.58 mM, and hence the reaction yield thereof was 45.1%. The concentration of the 6-aminocaproic acid was 0.028 mM, and hence the reaction yield thereof was 0.8%.

EXAMPLE 7

Reaction was carried out as in Example 1, thus attempting continuous production of ε-caprolactam through a rearrangement reaction of cyclohexanone oxime. The reaction conditions, however, were changed to the following.

Reaction Conditions
Temperature and pressure of carrier water: 475° C., 40 MPa
Flow rate of carrier water: 15.6 ml/min
Temperature and pressure of 21.9 mM substrate solution: 25° C., 40 MPa
Flow rate of 21.9 mM substrate solution: 4.4 ml/min
Temperature of high-temperature high-pressure water to be reacted: 375° C.
Pressure of high-temperature high-pressure water to be reacted: 40 MPa
Density of high-temperature high-pressure water to be reacted: 0.6096 g/cm$^3$
Flow rate of high-temperature high-pressure water to be reacted: 20.0 ml/min The cyclohexanone oxime substrate concentration after the mixing was 4.82 mM. The reaction time was 0.182 seconds, and the temperature throughout the reactor was constant, and hence it is inferred that the mixing took place within a short time of not more than 0.002 seconds. The aqueous solution after the reaction was examined using a high performance liquid chromatography-mass spectrometry apparatus, whereupon it was found that ε-caprolactam as a main product and 6-aminocaproic acid as a byproduct had been produced. Apart from that, only unreacted cyclohexanone oxime was detected, with cyclohexanone, which is the hydrolysis product of the raw material, not being detected at all. The concentration of the ε-caprolactam was 1.31 mM, and hence the reaction yield thereof was 27.2%. The concentration of the 6-aminocaproic acid was 0.023 mM, and hence the reaction yield thereof was 0.5%.

EXAMPLE 8

Reaction was carried out as in Example 1, thus attempting continuous production of ε-caprolactam through a rearrangement reaction of cyclohexanone oxime. The reaction conditions, however, were changed to the following.

Reaction Conditions
Temperature and pressure of carrier water: 475° C., 40 MPa
Flow rate of carrier water: 1.4 ml/min
Temperature and pressure of 21.9 mM substrate solution: 25° C., 40 MPa
Flow rate of 21.9 mM substrate solution: 0.6 ml/min
Temperature of high-temperature high-pressure water to be reacted: 375° C.
Pressure of high-temperature high-pressure water to be reacted: 40 MPa
Density of high-temperature high-pressure water to be reacted: 0.6096 g/cm$^3$
Flow rate of high-temperature high-pressure water to be reacted: 2.0 ml/min The cyclohexanone oxime substrate concentration after the mixing was 4.82 mM. The reaction time was 1.820 seconds, and the temperature throughout the reactor was constant, and hence it is inferred that the mixing took place within a short time of not more than 0.015 seconds. The aqueous solution after the reaction was examined using a high performance liquid chromatography-mass spectrometry apparatus, whereupon it was found that ε-caprolactam as a main product and 6-aminocaproic acid as a byproduct had been produced. Apart from that, only unreacted cyclohexanone oxime was detected, with cyclohexanone, which is the hydrolysis product of the raw material, not being detected at all. The concentration of the ε-caprolactam was 3.68 mM, and hence the reaction yield thereof was 76.3%. The concentration of the 6-aminocaproic acid was 0.132 mM, and hence the reaction yield thereof was 2.7%.

EXAMPLE 9

Figure 2:
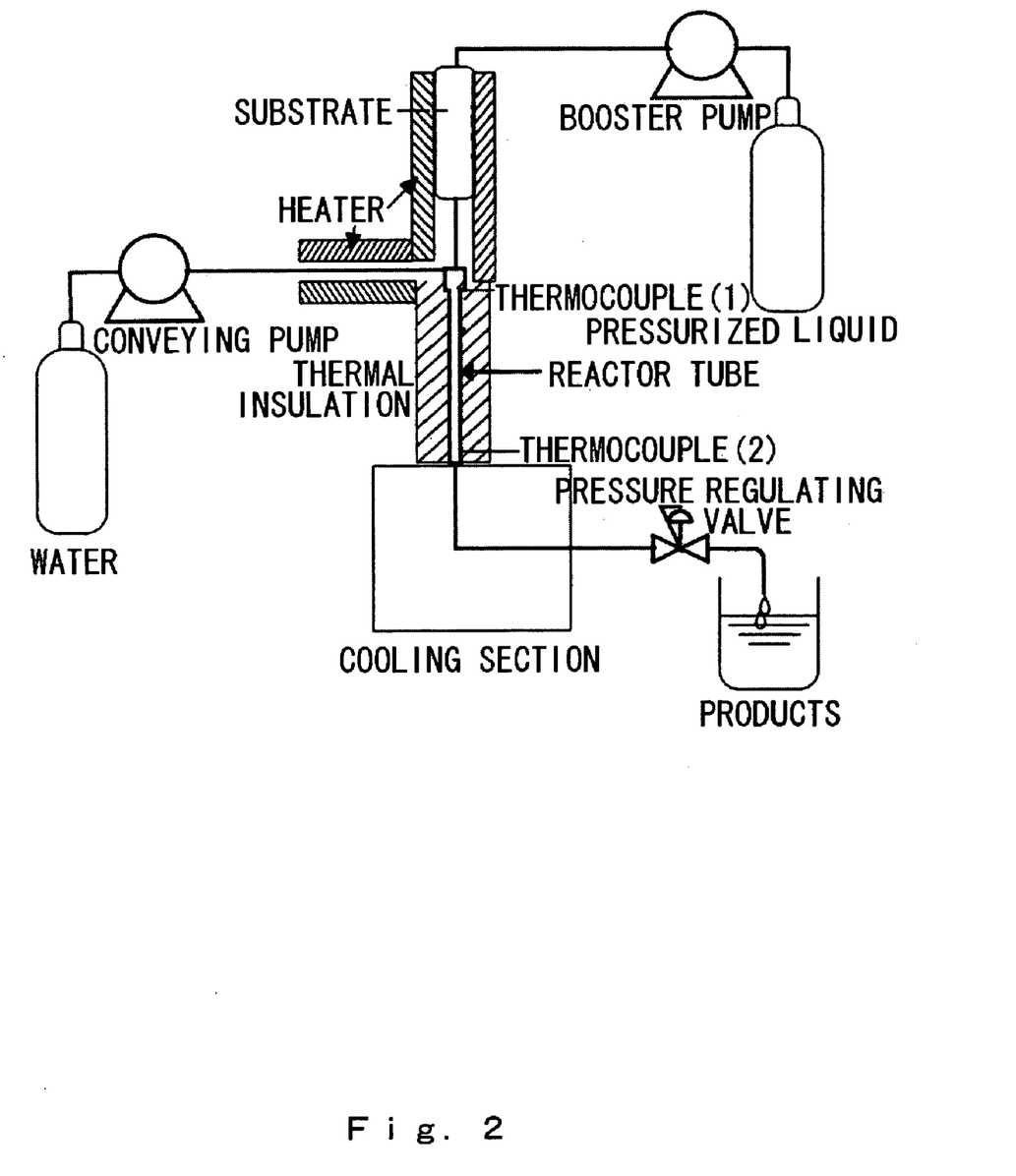
FIG. 2 shows an arrangement of a molten oxime introduction type flow type high-temperature high-pressure reaction apparatus having two conveying pumps used in the present invention.

Using a continuous type reaction apparatus as shown in FIG. 2, continuous production of ε-caprolactam through a rearrangement reaction was attempted by introducing a melt of cyclohexanone oxime (purity 97%) made by Aldrich Chemical Company, Inc. into high-temperature high-pressure water of temperature 350° C., pressure 30 MPa and density 0.6443 g/cm$^3$.

The material of the reactor was alloy C-276, and the internal diameter of the reactor was 4.68 mm and the length of the reactor was 200 mm, and hence the volume of the reactor was calculated to be 3.440 cm$^3$. Each of the prepared liquids to be introduced (i.e. the carrier water and the substrate melt) was injected in using a high-pressure pump. Distilled water from which dissolved oxygen had been driven out by bubbling with nitrogen gas was heated to produce carrier water at 357° C. and 30 MPa, and the carrier water was passed through at a flow rate of 24.6 ml/min. The cyclohexanone oxime was heated on 95° C. to prepare the substrate melt. The substrate melt was pressurized to 30 MPa using pressurized water and introduced into and thus mixed with the carrier water at the reactor inlet at a flow rate of 0.4 ml/min. The reaction temperature of the mixed solution measured by a thermocouple (1) installed 1 cm from the reactor inlet was 350° C., which matched the temperature measured by a thermocouple (2) at the reactor outlet, and hence it is inferred that the temperature throughout the reactor was constant, and that the carrier water and the substrate melt were mixed together homogeneously. The substrate concentration after the mixing was 141.6 mM. The reaction time was 5.165 seconds. It is thus inferred that the mixing and dissolution was completed within a short time of not more than 0.258 seconds. The aqueous solution after the reaction was examined using a high performance liquid chromatography-mass spectrometry apparatus, whereupon it was found that ε-caprolactam as a main product and 6-aminocaproic acid as a byproduct had been produced. Apart from that, only unreacted cyclohexanone oxime was detected, with cyclohexanone, which is the hydrolysis product of the raw material, not being detected at all. The concentration of the ε-caprolactam was 96.8 mM, and hence the reaction yield thereof was 68.4%. The concentration of the 6-aminocaproic acid was 2.1 mM, and hence the reaction yield thereof was 1.5%.

COMPARATIVE EXAMPLE 3

A thermocouple was connected to a SUS316 tubular reactor of internal diameter 8.7 mm and length 170 mm (internal volume 10.1 cm$^3$), and an experiment of synthesizing ε-caprolactam from cyclohexanone oxime using a batch type reaction method was carried out by rapidly raising the temperature thereof using a molten salt bath to 375° C. to react it for 3 minutes. Specifically, 3.5 g of distilled water and 0.5 g of cyclohexanone oxime were put into the reactor, and the reactor was sealed in a stream of nitrogen. The reactor was put into a molten salt bath the temperature of which had already been set to 375° C., whereby the reactor was heated to the set reaction temperature. The pressure at the reaction temperature was determined by calculation from the internal volume, the amount of water used, and the temperature, using the vapor pressure curve for water. After carrying out reaction for 3 minutes at 375° C., the reaction was stopped by putting the reactor into a cold water bath. The reaction pressure was 25 MPa, and the time taken for the temperature to rise to 375° C. was 29 seconds.

After the cooling the reaction mixture, the products in the reactor were recovered using water and chloroform, the organic solvent layer was separated off, and then the organic solvent was distilled off. The products were examined using mass spectroscopy, nuclear magnetic resonance spectroscopy and gas chromatography. The results of the analysis were that the yield of ε-caprolactam was 14.7% and the yield of cyclohexanone was 45.8%. With this batch type synthesis method, a large amount of cyclohexanone, which is the hydrolysis product of cyclohexanone oxime, was produced, and hence it is considered that the method is not suitable as an industrial process.

INDUSTRIAL APPLICABILITY

As described in detail above, the present invention relates to a continuous lactam production method in which a lactam is continuously synthesized without bringing about hydrolysis by introducing an oxime into flowing high-temperature high-pressure water, that is a continuous lactam production method in which a lactam is produced selectively from an oxime in high-temperature high-pressure water. According to the present invention, the following remarkable effects are attained: 1) a lactam can be produced selectively from an oxime by suppressing hydrolysis of the oxime in high-temperature high-pressure water; 2) a lactam can be produced within a short time by reacting an oxime under high temperature and high pressure; 3) a method of producing a lactam in which a catalyst is not used at all can be provided; and 4) the chemical substance production system which is environmentally friendly is provided.

What is claimed is:

1. A method for continuously producing caprolactam, comprising introducing an oxime into high-temperature high pressure water, raising the temperature of the oxime to put the oxime into a prescribed high-temperature high-pressure state within a short time, and subjecting the oxime to a rearrangement reaction to obtain the lactam;

wherein the temperature of the high-temperature high-pressure state is at least 375° C.;

wherein the pressure of the high-temperature high pressure water is at least 40 MPa;

wherein the raising the temperature of the oxime occurs in less than or equal to 0.3 seconds; and wherein the oxime has the formula (1)

wherein n is 3, and $R_1$ is hydrogen or an alkyl group.

2. The method for producing caprolactam according to claim 1, wherein a substrate aqueous solution having the oxime dissolved therein is introduced into the continuously flowing high-temperature high-pressure water, thus subjecting the oxime to the reaction in the prescribed high-temperature high-pressure state.

3. The method for producing caprolactam according to claim 1, wherein molten oxime is introduced into the continuously flowing high-temperature high-pressure water, thus subjecting the oxime to the reaction in the prescribed high-temperature high-pressure state.

4. The method for producing caprolactam according to any one of claims 1 through 3, wherein the oxime is subjected to the reaction in the prescribed high-temperature high-pressure state for a time of not more than 60 seconds.

5. The method for producing a lactam according to claim 4, wherein the oxime is subjected to the reaction in the prescribed high-temperature high-pressure state for a time of from 0.001 seconds to 60 seconds.

6. The method of claim 1, wherein $R_1$ is a radical selected from the group consisting of methyl, ethyl, propyl, and butyl.

* * * * *